US011857223B2

(12) United States Patent
Gregory et al.

(10) Patent No.: US 11,857,223 B2
(45) Date of Patent: Jan. 2, 2024

(54) MODULAR APPARATUS FOR EXTENDING AN EXISTING SPINAL CONSTRUCT

(71) Applicant: SPINE WAVE, INC., Shelton, CT (US)

(72) Inventors: Zachary Gregory, St. Louis, MO (US); Eugene Avidano, Stratford, CT (US); Dylan Freund, Carlsbad, CA (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

(21) Appl. No.: 17/580,091

(22) Filed: Jan. 20, 2022

(65) Prior Publication Data
US 2022/0233216 A1    Jul. 28, 2022

Related U.S. Application Data

(60) Provisional application No. 63/142,138, filed on Jan. 27, 2021.

(51) Int. Cl.
*A61B 17/70* (2006.01)
*A61B 17/00* (2006.01)

(52) U.S. Cl.
CPC ... *A61B 17/7052* (2013.01); *A61B 2017/00477* (2013.01)

(58) Field of Classification Search
CPC ............ A61B 17/7011; A61B 17/7043; A61B 17/7049–7052
See application file for complete search history.

(56) References Cited

U.S. PATENT DOCUMENTS

| 3,862,807 | A | 1/1975 | Doden et al. |
| 5,628,740 | A * | 5/1997 | Mullane ............. A61B 17/7041 606/307 |
| 5,672,176 | A | 9/1997 | Biedermann et al. |
| 5,797,911 | A | 8/1998 | Sherman et al. |
| 6,171,311 | B1 | 1/2001 | Richelsoph |
| 6,352,537 | B1 * | 3/2002 | Strnad ................ A61B 17/7007 606/276 |
| 6,485,491 | B1 | 11/2002 | Farris et al. |

(Continued)

OTHER PUBLICATIONS

International Search Report for PCT/US2022/013125, dated May 11, 2022.
Written Opinion for PCT/US2022/013125, dated May 11, 2022.

*Primary Examiner* — Eduardo C Robert
*Assistant Examiner* — Michelle C Eckman
(74) *Attorney, Agent, or Firm* — Hoffmann and Baron, LLP

(57) ABSTRACT

A modular apparatus for extending a rod in an existing spinal construct comprises a modular rod connector for attachment to the existing rod and a modular rod extender that may be selectively attached to the rod connector. Each rod connector includes a spherical head that is formed to have the same size and configuration such that any selected modular rod extender may be attached to a selected rod connector. Each rod connector comprises an attachment portion having an opening for receipt of a portion of the rod of an existing spinal construct. Each modular rod extender comprises an extender body including a common modular attachment feature at one end for receipt of the spherical head of the selected rod connector, and an extension rod extending from an opposite end to extend the existing spinal rod.

28 Claims, 9 Drawing Sheets

(56) References Cited

U.S. PATENT DOCUMENTS

| | | |
|---|---|---|
| 7,322,981 B2 | 1/2008 | Jackson |
| 7,476,239 B2 | 1/2009 | Jackson |
| 7,591,839 B2 | 9/2009 | Biedermann et al. |
| 7,875,065 B2 | 1/2011 | Jackson |
| 8,021,399 B2 | 9/2011 | Ritland |
| 8,337,532 B1 | 12/2012 | McLean et al. |
| 8,523,906 B2 | 9/2013 | McLean et al. |
| 8,556,938 B2 | 10/2013 | Jackson et al. |
| 8,758,411 B1 | 6/2014 | Rayon et al. |
| 8,876,869 B1 | 11/2014 | Schafer et al. |
| 9,320,546 B2 | 4/2016 | Keyer et al. |
| 9,763,702 B2 | 9/2017 | Schlaepher et al. |
| 9,907,574 B2 | 3/2018 | Jackson et al. |
| 10,076,361 B2 | 9/2018 | Jackson |
| 10,194,951 B2 | 2/2019 | Jackson et al. |
| 10,307,185 B2 | 6/2019 | Murray |
| 10,568,667 B2 | 2/2020 | Biester et al. |
| 10,736,666 B2 | 8/2020 | Prevost |
| 10,820,929 B2 | 11/2020 | Murray et al. |
| 11,109,895 B2 | 9/2021 | May et al. |
| 11,219,473 B2 | 1/2022 | May et al. |
| 2007/0135817 A1 | 6/2007 | Ensign |
| 2010/0298884 A1* | 11/2010 | Faizan .................. A61B 17/705 606/266 |
| 2011/0087287 A1* | 4/2011 | Reeder, Jr. .......... A61B 17/7011 606/264 |
| 2011/0106164 A1* | 5/2011 | Wilcox .............. A61B 17/7037 606/264 |
| 2011/0270325 A1* | 11/2011 | Keyer ................ A61B 17/7037 606/305 |
| 2013/0150895 A1* | 6/2013 | McLean ............ A61B 17/7011 606/278 |
| 2014/0121703 A1* | 5/2014 | Jackson ............... A61B 17/863 606/246 |
| 2017/0281237 A1* | 10/2017 | Murray ............. A61B 17/7049 |
| 2018/0014863 A1* | 1/2018 | Biester ............... A61B 17/7076 |
| 2019/0357944 A1 | 11/2019 | Jackson et al. |
| 2020/0289169 A1 | 9/2020 | McLean et al. |
| 2020/0337858 A1 | 10/2020 | Santiago |

\* cited by examiner

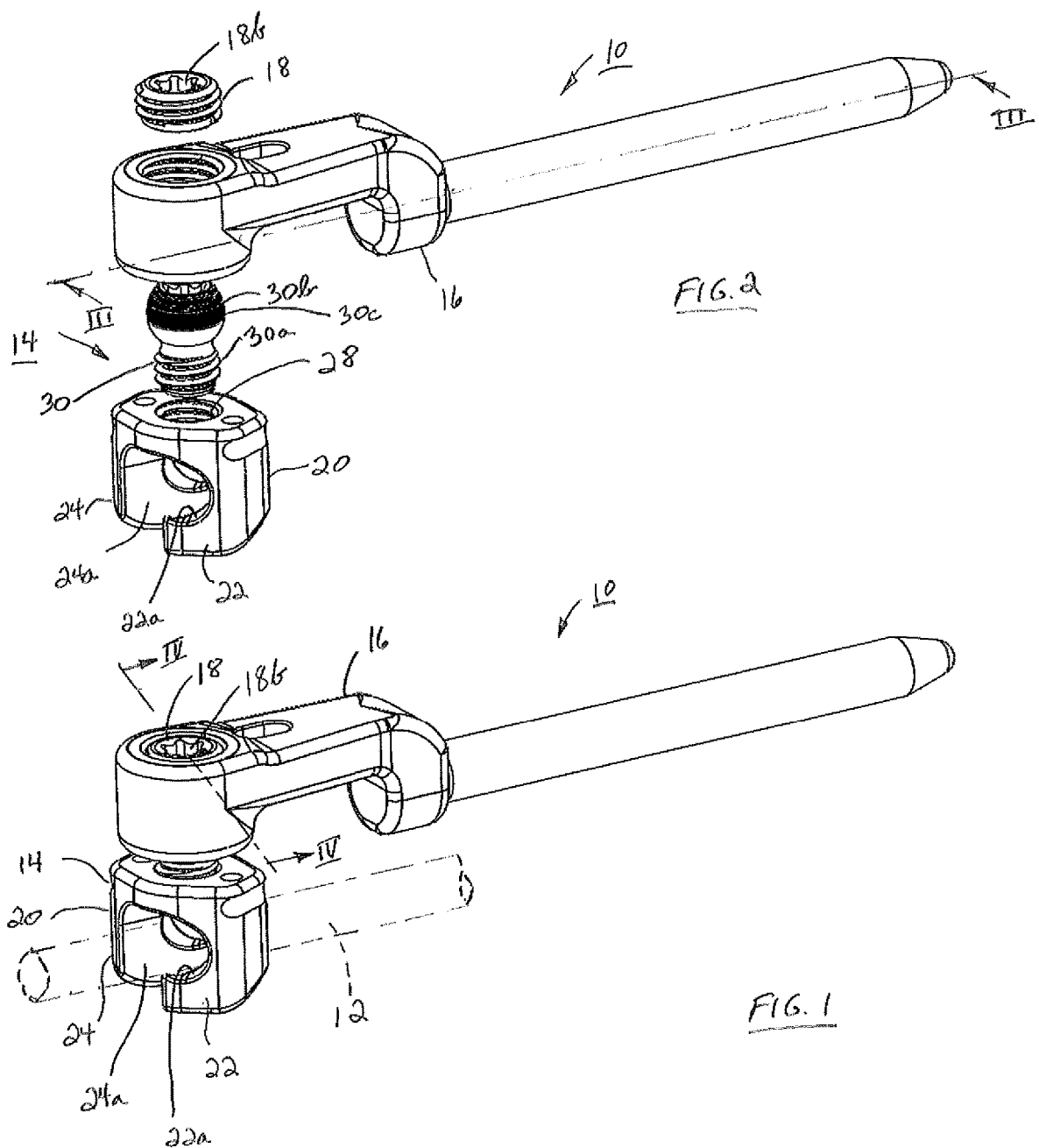

MODULAR APPARATUS FOR EXTENDING AN EXISTING SPINAL CONSTRUCT

CROSS-REFERENCE TO RELATED APPLICATION

This application claims the benefit of U.S. Provisional Patent Application No. 63/142,138, filed Jan. 27, 2021, the entire contents of which are incorporated by reference herein.

FIELD OF THE INVENTION

The present disclosure contemplates a spinal surgery construct, and more particularly a modular apparatus for extending an existing spinal construct, and procedures for achieving such modular extension.

BACKGROUND OF THE INVENTION

An emerging trend in spinal fixation is an increased incidence of adjacent disc degeneration subsequent to a previous fixation or fusion. This subsequent degeneration often requires fixation or fusion of additional levels of the spine. It is common in current techniques to expose the entire prior construct to access all of the existing bone fasteners to permit removal of the connecting member spanning the fasteners. The connecting member is removed and replaced with a longer member, such as a rod, to engage an additional bone fastener added at the new levels to be instrumented.

This exposure of the prior fixation construct disrupts the existing construct complicating and lengthening the surgical procedure for adding the additional level of fixation. Such techniques are particularly problematic for a fixation construct spanning three or more vertebral levels. As such, there is a need for a device and method that facilitates the addition of further levels of fixation.

Several recent advancements have been disclosed that describe the extension of existing spinal constructs with minimal disruption to the existing construct. One example is shown in commonly assigned U.S. Pat. No. 8,657,826, entitled "Apparatus and Devices for Percutaneously Extending an Existing Construct", issued to McLean et al. on Feb. 25, 2014 (the '826 Patent). The device disclosed in the '826 Patent includes a rod connector comprising a lower portion having a pair of spaced hooks for engaging an existing spinal rod and an upper portion defining a yoke receiving an additional rod to extend the existing construct. Another example includes commonly assigned U.S. Pat. No. 8,523,906, entitled "Apparatus and Devices for Percutaneously Extending an Existing Construct", issued to McLean et al. on Sep. 3, 2013 (the '906 Patent). The device disclosed in the '906 Patent includes a rod connector comprising a lower portion having a pair of spaced hooks for engaging an existing spinal rod and an upper portion having an integral additional rod to extend the existing construct. The entire contents of the '826 Patent and the '906 Patent are incorporated herein by reference.

A further trend in spinal construct extension technology is the evolution of modularity. Modularity allows a portion of the extension construct to be attached to an existing spinal structure with a separate modular portion configured to include a spinal rod extension attached to the first portion. This permits greater flexibility in supplying and choosing spinal implants and fixation components that are properly sized and dimensioned for a particular anatomy. One known example is described in U.S. Pat. No. 10,307,185, entitled "Revision Connectors, Systems, and Methods Thereof", issued to Patrick Murray on Jun. 4, 2019 and assigned on its face to Globus Medical, Inc. While this approach represents an improvement in revision techniques and devices, it would be advantageous to provide a cost-effective modular revision system that is simple and easy for a surgeon to use.

SUMMARY OF THE INVENTION

It is an object of the invention to provide an improved modular rod extender for extending a rod in an existing spinal construct.

It is another object of the invention to provide an improved modular apparatus for extending a rod in an existing spinal construct that includes a rod connector attachable to the existing rod and a modular rod extender that has a modular attachment feature at one end for attachment to the rod connector and an extension rod extending from the other opposite end.

DESCRIPTION OF THE FIGURES

FIG. 1 is a perspective view of a modular apparatus for extending an existing ipsilateral spinal construct comprising a rod connector and a modular rod extender in accordance with an embodiment of the invention.

FIG. 2 is an exploded perspective of the modular apparatus of FIG. 1.

DESCRIPTION OF THE EMBODIMENTS

Figure 3:
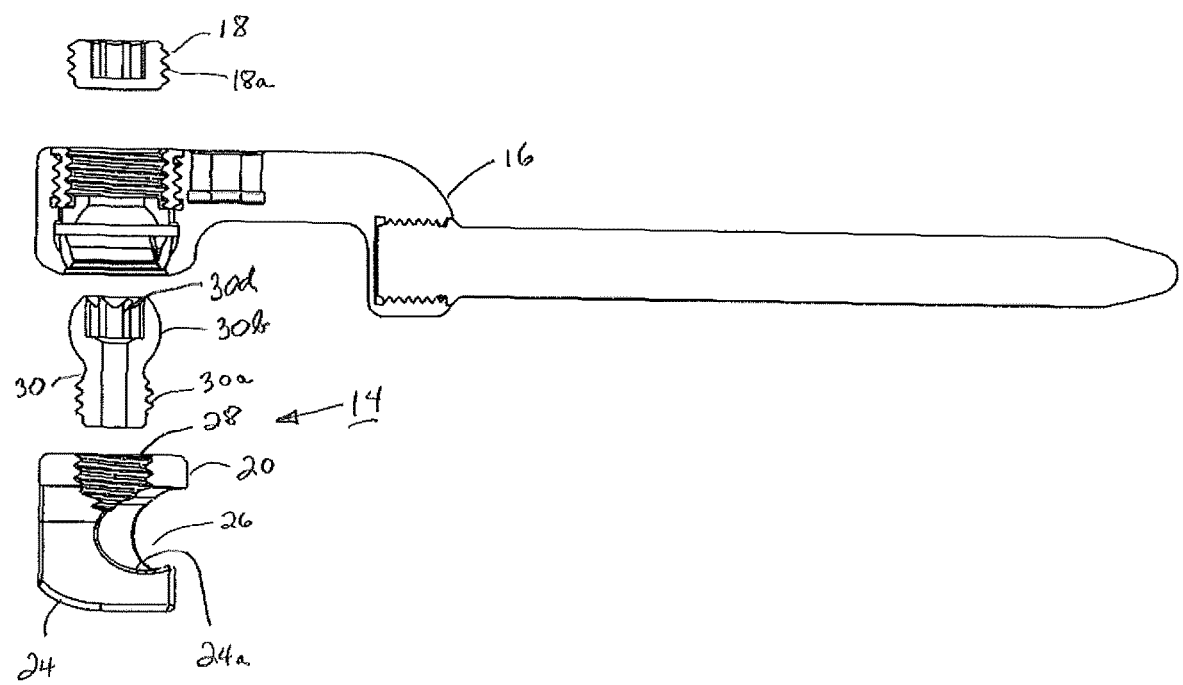
FIG. 3 is a longitudinal cross-sectional view of the exploded view of the modular apparatus as seen along viewing lines III-III of FIG. 2.

For the purposes of promoting an understanding of the principles of the invention, reference will now be made to the embodiments illustrated in the drawings and described in the following written specification. It is understood that no limitation to the scope of the invention is thereby intended.

It is further understood that the present invention includes any alterations and modifications to the illustrated embodiments and includes further applications of the principles of the invention as would normally occur to one skilled in the art to which this invention pertains.

Referring to FIGS. 1-2 a modular apparatus 10 is shown for extending an existing spinal construct that includes an existing spinal rod 12 (shown in phantom) so as to increase the level of spinal fixation in a patient having previously undergone spinal fusion or other spinal surgery. The modular apparatus 10 generally comprises a rod connector 14, a modular rod extender 16 and a locking element is. In one arrangement, locking element 18 is a set screw that has external threads 18a. In use, the existing spinal rod 12 and the modular rod extender 16 are typically located ipsilaterally in the spine. Spinal rod 12 is an existing spinal construct in the sense that it has been installed prior to the installation of the modular apparatus 10, which means that existing spinal rod 12 may have been placed in a previous surgical procedure or may be placed during the same surgical procedure as, but prior to, modular apparatus 10. As will become more evident, modular apparatus 10 is an enhancement over the rod connector shown and described in the above referenced, commonly assigned '906 Patent which comprises a lower portion that is attachable to an existing spinal rod and an upper portion with an integral additional spinal rod that is pre-attached polyaxially to the lower portion. As will be described, rod connector 14 and modular rod extender 16 are separate components that are attached in a modular fashion, for example during a surgical procedure, to form the modular apparatus 10.

Figure 4:
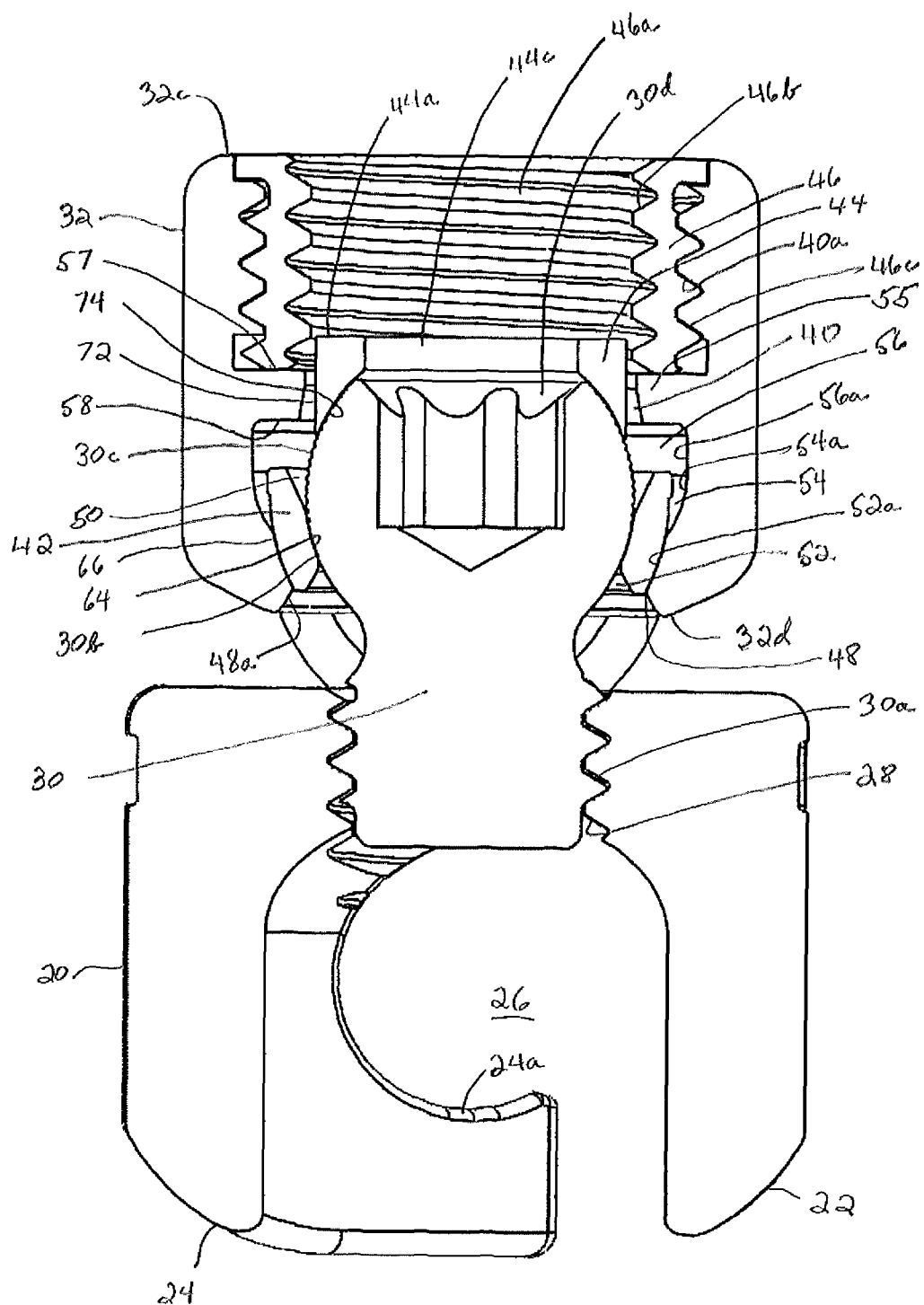
FIG. 4 is an enlarged cross-sectional view of the modular apparatus as seen along viewing lines IV-IV of FIG. 1.

Turning now also to FIGS. 3-4, details of rod connector 14 are described. Rod connector 14 comprises an attachment portion 20 that includes, in one arrangement, a pair of spaced hooks 22 and 24 each of which includes a respective projecting rod engagement member 22a and 24a. Hooks 22 and 24 are spaced from each other at a distance defining an opening 26 that allows the existing rod 12 to be received therebetween. A threaded opening 28 is formed into attachment portion 20 opposite hooks 22 and 24, with threaded opening 28 being in communication with rod receiving opening 26. An elongate post 30 has a lower threaded portion 30a and an upper head 30b having an outer surface formed as a truncated sphere. Head 30b may have annular ridges 30c as seen in FIGS. 2 and 4, or a suitable serrated surface to assist in the securement of post 30 to modular rod extender 16, as will be described. A socket 30d may be included to extend into upper head 30b, socket 30d being in a suitable configuration such as a hexalobe to receive a tool for attaching rod connector 14 to existing spinal rod 12 and for securing rod connector 14 thereto. Threaded portion 30a is threadably received in threaded opening 28 of attachment portion 20 to form rod connector 14.

Figure 5:
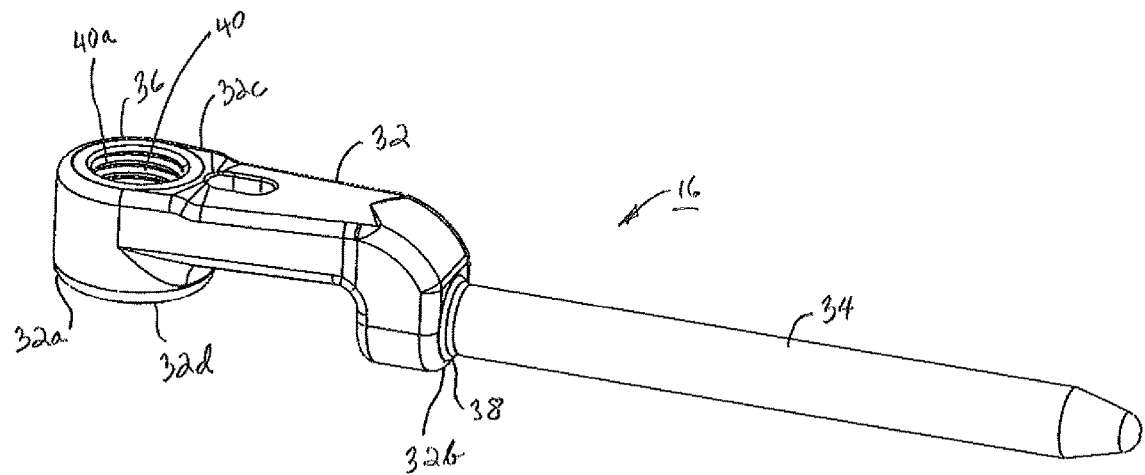
FIG. 5 is a perspective view of the modular rod extender of the modular apparatus of FIG. 1.
Figure 6:
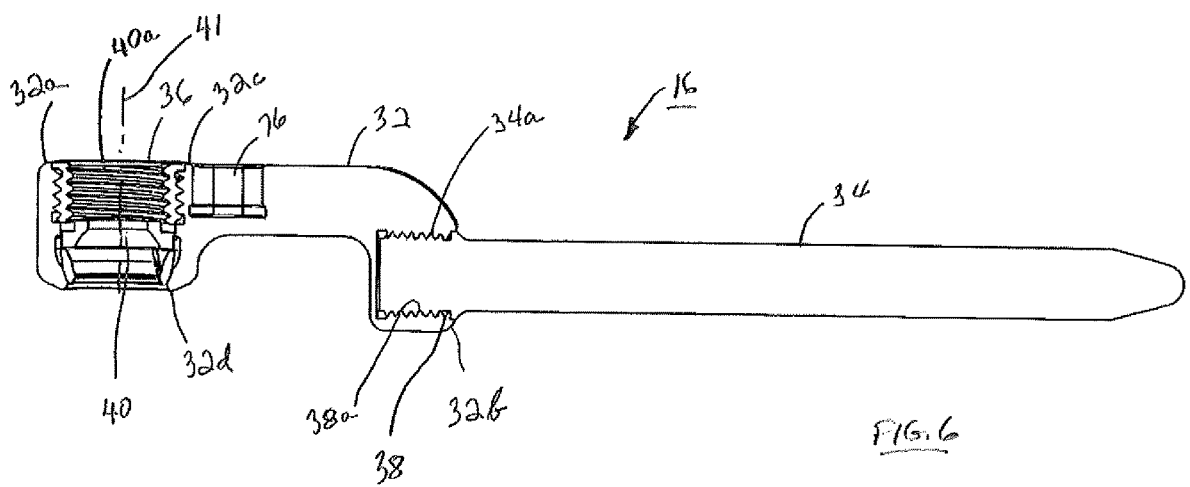
FIG. 6 is a longitudinal cross-sectional view of the modular rod extender of FIG. 5.

Turning in addition to FIGS. 5-11, further details of modular rod extender 16 are described. Modular rod extender 16 comprises an extender body 32 and an extension rod 34 attached thereto. Extender body 32 comprises a modular attachment feature 36 at one end 32a and a rod attachment feature 38 at an opposite end 32b. Modular attachment feature 36 comprises a central bore 40 formed through a top surface 32c and a bottom surface 32d of extender body 32, a socket collar 42, a crown 44 and a retention insert 46. Central bore 40 extends along an axis 41 as shown in FIG. 6 and has internal threads 40a in an upper portion adjacent top surface 32c. Extension rod 34 is elongate and serves to provide an additional rod to extend the existing construct from existing spinal rod 12 to another spinal level where it may be attached to a further pedicle screw or other suitable bone anchor. Extension rod 34 is attached to extender body 32 by rod attachment feature 38 as shown in FIGS. 5-6, which may include external threads 34a threadably engaging internal threads 38a formed into extender body 32 at end 32b. Extension rod 34 may be welded to extender body 32 subsequent to threaded engagement thereto to further secure the connection. Alternatively, extender body 32 and extension rod 34 may be formed as an integral, one-piece member. As shown in FIGS. 5-6, extender body 32 and extension rod 34 form an in-line modular rod extender 16 wherein the longitudinal axis of extension rod 34 is axially aligned with extender body 32 and, particularly with central bore 40.

Figure 8:
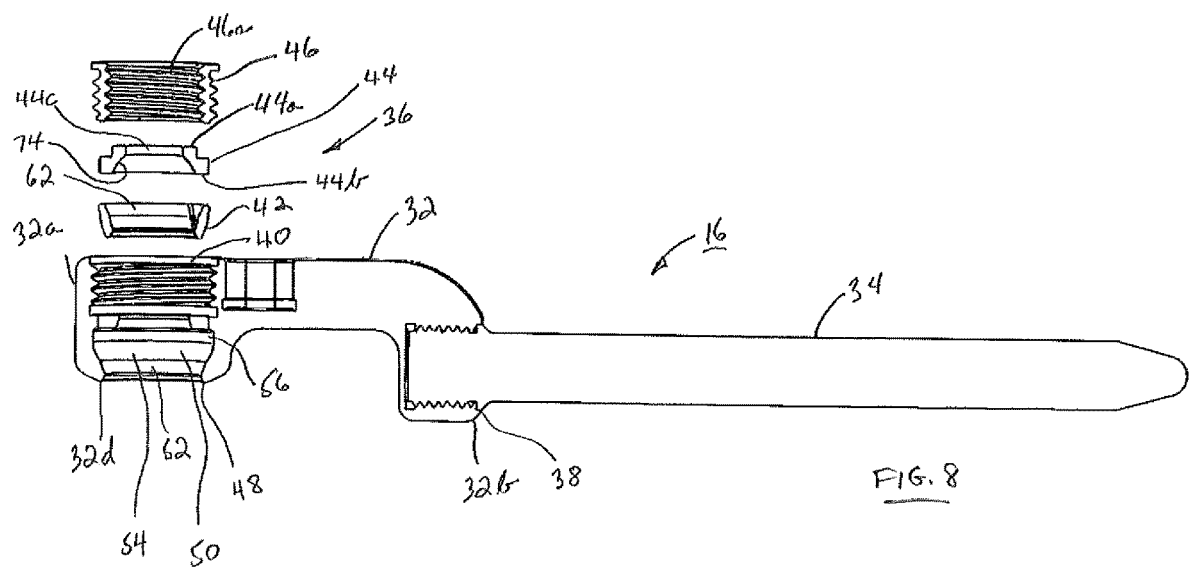
FIG. 8 is a longitudinal cross-sectional view of the exploded view of the modular rod extender of FIG. 7.
Figure 7:
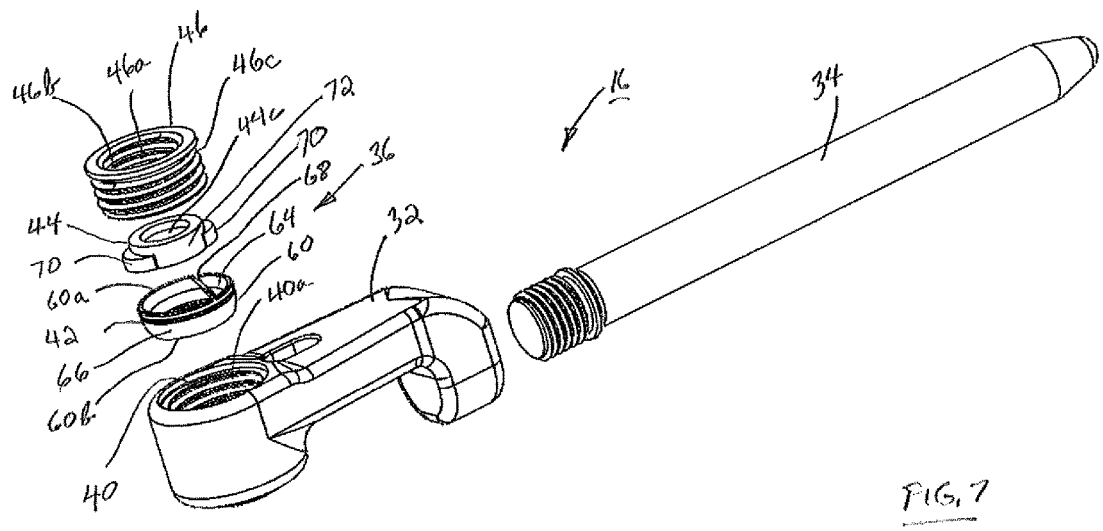
FIG. 7 is an exploded perspective view of the modular rod extender of FIG. 5.

Referring now to FIGS. 4 and 7-8, further details of central bore 40 forming a portion of modular attachment feature 36 are described. The lower portion of central bore 40 adjacent bottom surface 32d is formed to have a lower opening 48 and a lower interior cavity 50, lower interior cavity 50 communicating with lower opening 48 and central bore 40. Lower opening 48 has a diameter greater that the maximum diameter of spherical outer surface of post head 30b such that post 30 may be bottom loaded through lower opening 48. An outwardly downwardly flared chamfer 48a may be formed at the bottom of lower opening 48. Lower interior cavity 50 has a first region 52, a second region 54 and a third region 56. First region 52 communicates with lower opening 48 and preferably has a first partially spherical internal surface 52a having a first radius of curvature. First region 52 has a portion that is diametrically wider than the diameter of opening 48. Second region 54 communicates with first region 52 and preferably has a second partially spherical internal surface 54a having a second radius of curvature. The second radius of curvature of second internal surface 54a is in one arrangement less than the first radius of curvature of first internal surface 52a. Second region 54 has a portion that is diametrically wider than the widest diameter of region 52. Third region 56 communicates with second region 54 and preferably has a cylindrical internal surface 56a. Third region 56 is substantially as wide as the widest portion of second region 54 and greater than the diameter defining central bore 40. A ledge 55 extends radially interiorly within extender body 32, ledge 55 having an upper contact surface 57 and a lower surface defining an interior stop surface 58. Third region 56 terminates interiorly of lower interior cavity 50 at interior stop surface 58 that extends transversely relative to cylindrical internal surface 56a. Formation of the second region 54 and third region 56 allows for expansion of socket collar 42, as will be described.

Referring again to FIGS. 4 and 7-8, details of socket collar 42 are described. Collar 42 comprises a ring 60 of generally circular configuration having a generally circular central opening 62. Ring 60 includes a top surface 60a and a bottom surface 60b that in one arrangement are substantially parallel. Opening 62 preferably has a partially spherical internal surface 64 having a radius of curvature, $R_1$. The radius of curvature of internal partially spherical surface 64 is in one arrangement substantially the same as the radius of curvature of the outer spherical surface 30b of post 30. Ring 60 has an outer surface 66 that preferably includes a partially spherical external surface that has a radius of curvature, $R_2$ that is greater than the radius of curvature, $R_1$ of internal surface 64. The radius of curvature of external partially spherical surface 66 is in one arrangement substantially the same as the radius of curvature of first partially spherical surface 52a in the lower interior cavity 50 at the lower portion of central bore 40. As such, socket collar 42 cannot pass through the lower portion of central bore 40. In a preferred arrangement, ring 60 is split as defined by a gap 68 as shown in FIG. 7 that extends angularly through ring 60. Gap 68 allows a certain amount of radial expansion and contraction of ring 60. In the unexpanded condition of socket collar 42, opening 62 has a dimension that is less than the maximum diameter of head 30b of post 30 such that head 30b may not pass therethrough unless socket collar 42 is expanded. Further details of socket collar 42 and its function are set forth in commonly assigned U.S. patent application Ser. No. 16/843,160, issued as U.S. Pat. No. 11,219,470, entitled "Modular Tensioned Spinal Screw", filed by Eugene Avidano on Apr. 8, 2020, the entire contents of the '160 application being incorporated herein by reference.

Referring yet again to FIGS. 4 and 7-8, further the details of crown 44 are described. Crown 44 is of generally cylindrical configuration having an upper end 44a and an opposite lower end 44b with a bore 44c extending therethrough. As best seen in FIG. 7, crown 44 includes a pair of lobes 70 that project outwardly radially oppositely from crown 44 and provide crown alignment, as will be described. Exteriorly between lobes 70 crown 44 includes a generally cylindrical body 72 having a diameter slightly smaller than the diameter defining central bore 40. A lower interior surface 74 at the lower end 44b of crown 44 is formed to have a partially spherical concave surface having a radius of curvature that in one arrangement is substantially the same as the radius of curvature of the outer spherical surface of past head 30b.

Referring still further to FIGS. 4 and 7-8, additional details of retention insert 46 are described. Retention insert 46 is generally cylindrical having a central opening 46a extending therethrough. In one arrangement, retention insert 46 has internal threads 46b in central opening 46a and external threads 46c extending on an outer surface of retention insert 46. Internal threads 46b are configured to threadably receive external threads 18a of locking element 18 while external threads 46c on retention insert 46 are configured for threadable receipt into internal threads 40a of central bore 40, as will be described.

Figure 9:
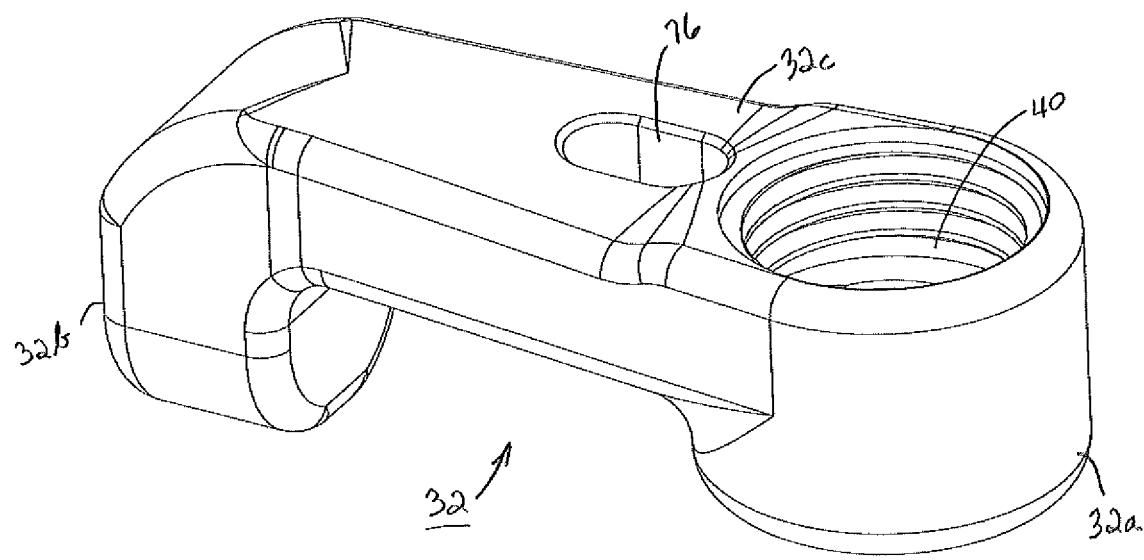
FIG. 9 is a top perspective view of the extender body of the modular rod extender of FIG. 5.
Figure 10:
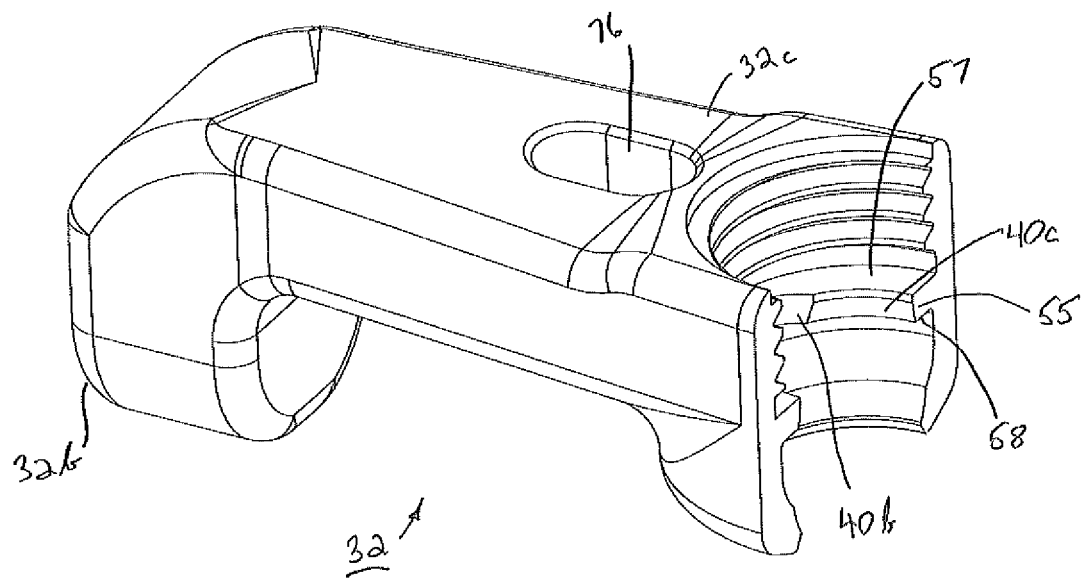
FIG. 10 is the view of FIG. 9 with a portion removed to reveal inner structural details of the extender body.
Figure 11:
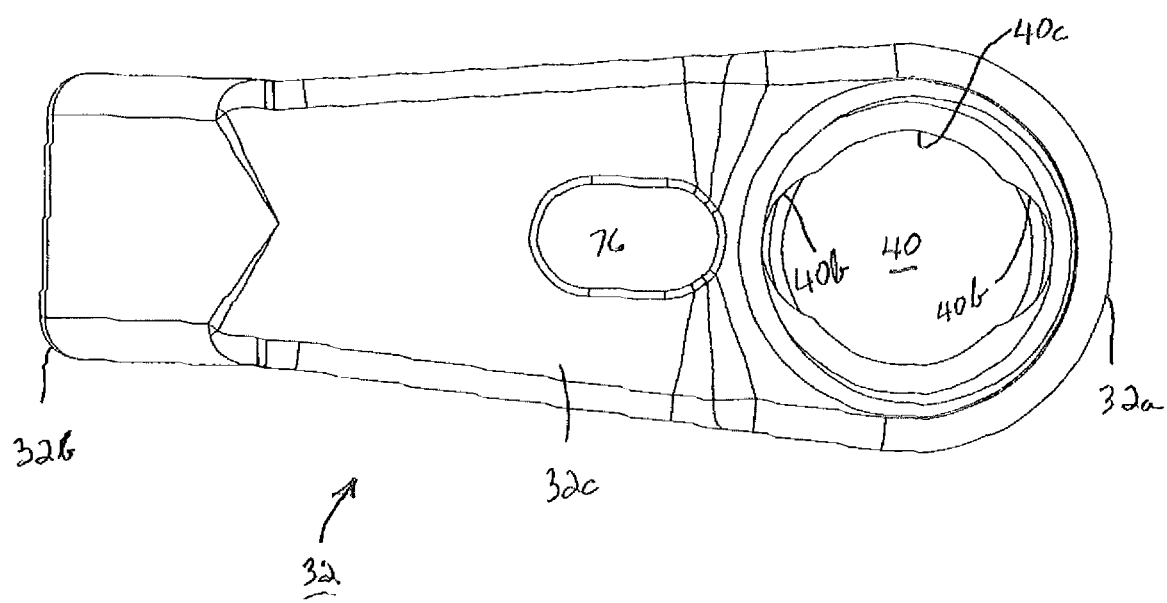
FIG. 11 is a top plan view of the extender body of FIG. 9.

Turning now to FIGS. 9-11, additional details of extender body 32 are described. As shown particularly in FIGS. 10 and 11, central bore 40 has a pair of opposing cutouts 40b formed into an interior surface 40c that has a diameter defining central bore 40. Cutouts 40b are configured to receive respective lobes 70 of crown 44 in assembly, as will be described. Top surface 32c may be formed to include an opening 76 that is configured to receive a portion of an insertion instrument that is used to introduce modular rod extender 16 to the surgical site. In one arrangement, opening 76 may have an oval shape so as to provide suitable alignment between the insertion instrument and modular rod extender 16. Opening 76 may be formed to extend partially into extender body 32 through top surface 32c (see FIG. 6). Alternatively, opening 76 may be formed to extend fully through extender body 32.

The components of rod connector 14 and modular rod extender 16 may comprise any suitable biocompatible material, including but not limited to titanium, cobalt chrome and PEEK.

Having described details of the components of modular apparatus 10, the assembly of the components to form modular rod extender 16 is now described with particular reference to FIGS. 4 and 6-8. Socket collar 42, crown 44 and retention insert 46 are sequentially introduced into central bore 40 of extender body 32 in a top-loading process. Socket collar 42, introduced initially, is rotated 90° so that top surface 60a and bottom surface 60b of socket collar 42 respectively face internal threads 40a within central bore 40. In this manner socket collar 42, with slight contraction if necessary, is capable of passing through central bore 40 until socket collar 42 reaches the wider lower interior cavity 50 adjacent bottom surface 32d of extender body 32. Socket collar 42 is then rotated 90° within lower interior cavity 50 to the position shown in FIG. 4 wherein socket collar 42 rests floatingly on first partially spherical internal surface 52a of lower interior cavity region 52. Crown 44 is then introduced into inner central bore 40 in a top-loading process whereby lobes 70 are oriented in alignment with cutouts 40b, as shown in FIGS. 10 and 11. In this orientation, crown 44 is in a fixed alignment with extender body 32 and will be prevented from rotation and thereby remain in a fixed position during modular attachment of rod extender 16 to rod connector 14, as will be described. In certain instances, crown 44 may be formed of a softer material such as commercially pure titanium (CP Ti). This would allow crown 44 to lock against head 30b of rod connector post 30 during use, as will be described.

Retention insert 46 is then introduced into central bore 40 by threading external threads 46c into internal threads 40a of central bore 40. Upon reaching the proper position within central bore 40 when retention insert 46 bottoms out on upper contact surface 57 of ledge 55, insert 46 is secured therein by a suitable process, such as by welding. As so secured, retention insert 46 is fixed in position relative to central bore 40 and covers lobes 70 of crown 44, effectively retaining socket collar 42 and crown 44 within central bore 40. With retention insert 46 secured in such a fixed position and with socket collar 42 being prevented from passing out through the bottom of central bore 40, both socket collar 42 and crown 44 may move up and down to a degree within central bore 40 until post 30 is modularly received. It should be appreciated that retention insert 46 may also be formed, for example, as a bushing that is welded in place, thereby potentially eliminating the need for external threads 46c and internal threads 40a within central bore 40.

In use for spinal surgery, a kit may be provided comprising a plurality of rod connectors 14 and a plurality of modular rod extenders 16. The rod connectors 14 may be modular and configured to each have a different rod receiving opening 26 to accommodate existing spinal rods 12 of different diameter. The modular rod extenders 16 may have extension rods 34 of different lengths and different diameters to accommodate different surgical procedures or patient anatomies. However, the heads 30b of each rod connector post 30 are commonly formed to have a spherical surface having the same size and configuration such that any selected modular rod extender 16 may be attached to a selected rod connector 14. It should therefore be appreciated that the subject modular apparatus 10 provides flexibility and options for the surgeon in selecting appropriate spinal fixation implants depending upon surgical circumstances and anatomies in a cost-effective manner.

After selection of a suitable rod connector 14 and a suitable modular rod extender 16, the chosen rod connector 14 is placed on the existing spinal rod 12 by introducing the existing spinal rod 12 into rod receiving opening 26. Rod connector 14 is rotated such that hooks 22 and 24 straddle existing spinal rod 12. Such placement and rotation of rod connector 14 may be achieved by a suitable instrument. Rod connector 14 may be slid axially along existing spinal rod 12 to a position determined to be appropriate by the surgeon. Post 30 is then tightened against existing spinal rod 12 by a tool engaged with socket 30d to cause rod engagement members 22a and 24a to engage and securely lock the chosen rod connector 14 onto the existing spinal rod 12. A chosen modular rod extender 16 may then be pushed by an appropriate instrument on to the spherical outer surface of head 30b of post 30 to form the assembled modular apparatus as shown in FIG. 1, prior to placement of locking element 18. In some circumstances, locking element 18 may be pre-attached to modular rod extender 16 before modular attachment to rod connector 14. Upon downward movement of modular rod extender 16 onto head 30b, head 30b moves socket 42 axially upwardly into the wider regions 54 and 56 of lower interior cavity 50 of central bore 40 since head 30b cannot pass through socket collar opening 62 in the relaxed unexpanded condition. Upon further relative movement of head 30b upwardly socket collar top surface 60a will ultimately contact interior stop surface 58 within lower interior cavity 50. Continued movement of modular rod extender 16 downwardly will then push head 30 into and through socket collar opening 62 to expand the socket collar 20 radially via the gap 68.

Once the spherical head 30b of post passes through collar opening 62 an audible click may be heard together with a tactile feel as socket collar 42 returns to its non-stressed radius. At this point, socket collar 42 will be disposed below the maximum diameter of post head 30b, as shown in FIG. 4. In such assembled but unlocked configuration, rod extender 16 may be moved polyaxially and rotationally on post head 30b relative to rod connector 14. It should also be appreciated that while a chosen rod connector 14 may be initially separately placed on and secured to an existing spinal rod 12 as described, where appropriate access to socket 30d of post 30 through central bore 40 is provided, the chosen rod connector 14 and the chosen modular rod extender 16 may be pre-attached and jointly placed on existing spinal rod 12.

To tighten modular rod extender 16 to rod connector 14, locking element 18 may then be threaded into internal threads 46b of retention insert 46. Locking element 18 includes an interior socket 18b (see FIGS. 1 and 2) formed to have a hexalobe shape or other suitable configuration for receipt of a driver instrument (not shown) for threading locking element 18 into internal threads 46b of retention insert 46. Upon tightening, locking element 18 will engage upper end 44a of crown 44. Continued tightening will push crown 44 further downward within central bore 40 causing lower concave surface 74 of crown 44 to forcibly engage head 30b of post 30. This in turn moves post head 30b further downward as extender body 32 moves relatively upward. Such relative movement causes the bottom of post head 30b to forcibly engage socket collar 42 and wedge socket collar 42 rigidly against first partially spherical internal surface 52a at the lower end of central bore 40. Upon complete tightening of locking element 18, modular rod extender 16 and rod connector 14 are securely coupled, thereby preventing relative movement therebetween. Annular ridges 30c on post head 30b enhance the security of the connection between post head 30b and socket collar 42.

Having described a particular arrangement of modular apparatus 10 wherein modular rod extender 16 has an extension rod 34 in-line with modular attachment feature 36, two alternative embodiments are now described. The first alternative arrangement is shown and described with reference to FIGS. 12 and 13. A modular rod extender 116 comprises elongate extension rod 34 attached to a curved extender body 132 by rod attachment feature 38. Curved extender body 132 is substantially the same in all respects as modular extender body 32, including modular attachment feature 36, except that it is curved in a plane transverse to the direction of central bore 40. Such curvature results in a lateral offset orientation of the longitudinal axis of extension rod 34 relative to central bore 40. The curvature of curved extender body 132 may be formed in a manner to allow extension rod 34 to be positioned closer to the midline axis of the patient's spine or in an opposite manner to allow extension rod 34 to be positioned farther away from the patient's midline axis. Such a curved extender body 132 is configured to provide a lower profile extension of an existing spinal construct.

Figure 12:
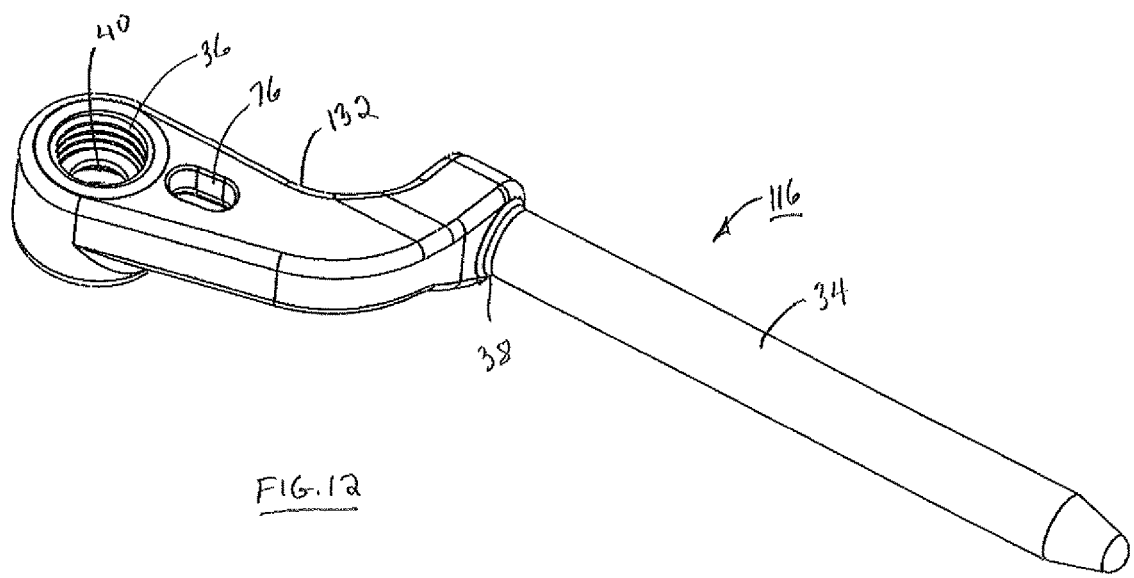
FIG. 12 is a top perspective view of a modular rod extender in accordance with a second embodiment having an offset extension rod.
Figure 13:
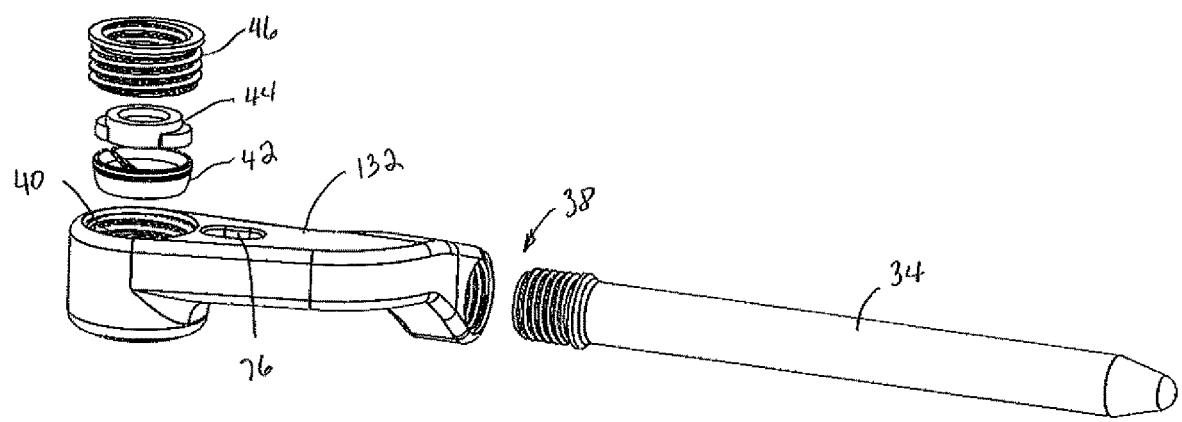
FIG. 13 is an exploded view of the alternative modular rod extender of FIG. 12.
Figure 14:
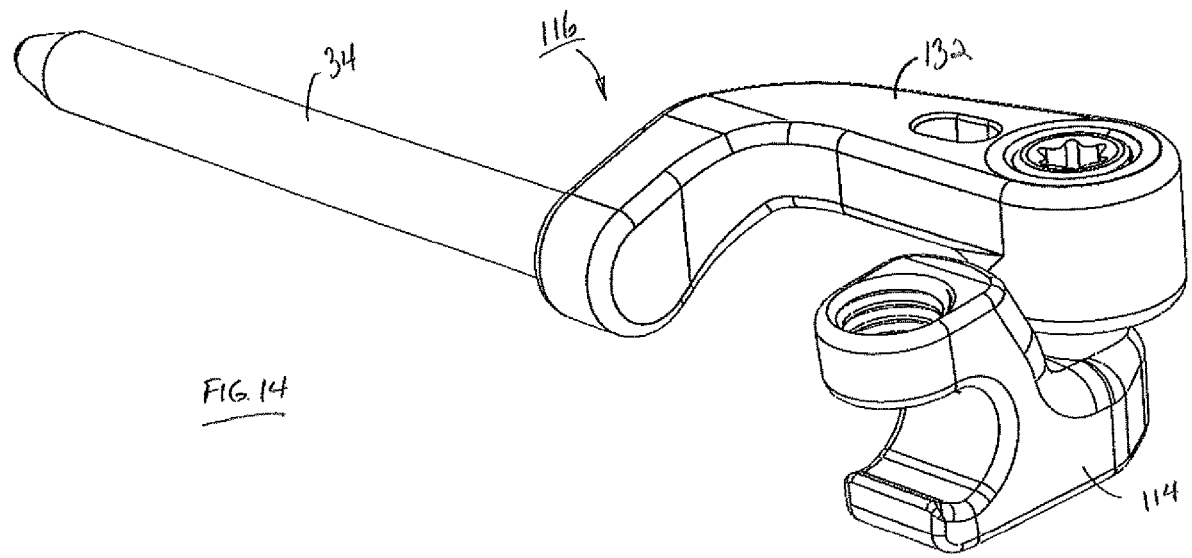
FIG. 14 a top perspective view of the modular rod extender of FIG. 12 having an offset extension rod attached to a lateral rod connector in accordance with a third embodiment.
Figure 15:
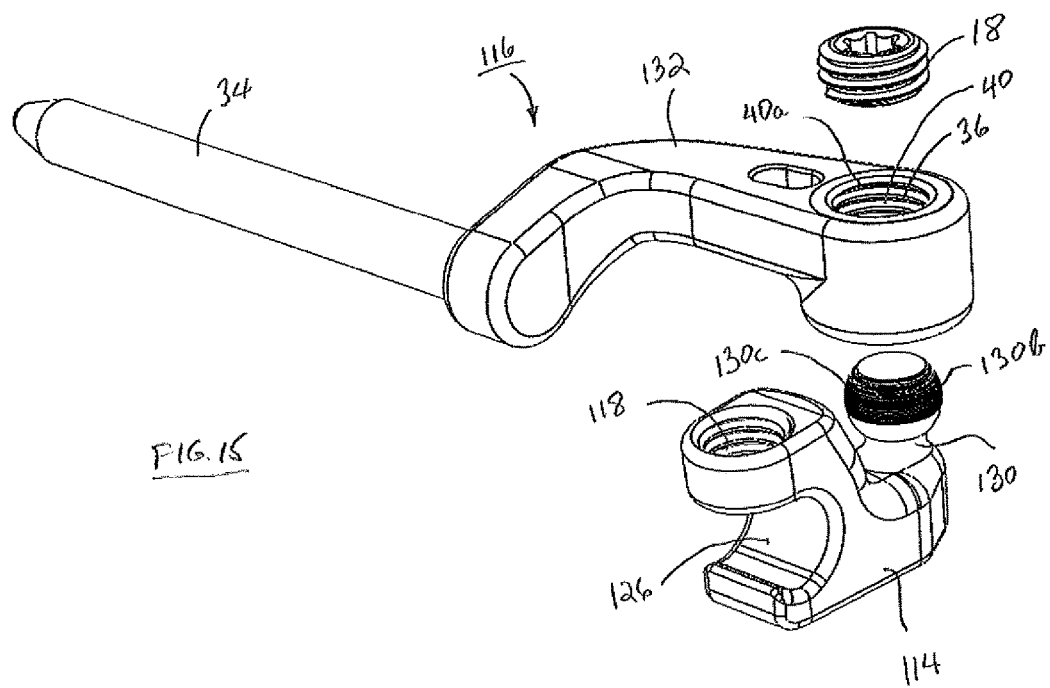
FIG. 15 is an exploded view of the offset modular rod extender and lateral rod connector of FIG. 14.

Turning now to FIGS. 14 and 15 the second alternative arrangement is shown and described. In this embodiment modular rod extender 116, as described with reference to FIGS. 12 and 13, is modularly attachable to a lateral rod connector 114. Lateral rod connector 114 has a side opening 126 for lateral receipt of an existing spinal rod 12. Lateral rod connector 114 may be suitably attached to existing spinal rod 12 by a fastening element (not shown) threadably engaging threaded opening 118. Lateral rod connector 114 includes an elongate post 130 similar to post 30 of rod connector 14. Post 130 has an upper head 130b having an outer surface formed as a truncated sphere, which may include annular ridges 130c or other suitable high friction surface. Post head 130b is received in modular attachment feature 36 of modular rod extender 116 in the same manner as post 30 of rod connector 14 is received in modular rod extender 16, as described above. Initial attachment is unlocked and allows polyaxial and rotational movement of modular rod extender 116 on post head 130b, relative to lateral rod connector 114. Modular rod extender 116 may be subsequently locked in a desired orientation to lateral connector 114 by advancing locking element 18 into threads 40a central bore 40. This arrangement is configured to allow not only for a lower profile extension of existing spinal rod 12, but also a substantial co-axial orientation of extension rod 34 relative to an existing spinal rod 12, while potentially passing around existing spinal constructs.

While the invention has been illustrated and described in detail in the drawings and foregoing description, the same should be considered as illustrative and not restrictive in character. It is understood that only the preferred embodiments have been presented and that all changes, modifications, and further applications that come within the spirit of the invention are desired to be protected.

What is claimed is:

1. A modular rod extender for extending a rod in an existing spinal construct, comprising:
    an extender body comprising a modular attachment feature at one end and an extension rod extending from an opposite end, said modular attachment feature comprising:
    a central bore extending along an axis through a top surface and a bottom surface of said extender body, said central bore having a lower portion and an upper portion, a ledge extending radially interiorly within said extender body, said ledge including an interior surface defining said central bore and having an interior diameter, said ledge including an upper contact surface facing said upper portion of said central bore and a lower surface facing said lower portion of said central bore, said upper portion having an upper opening with an innermost diameter greater than said interior diameter of said interior surface, said lower portion having a lower opening adjacent said bottom surface and a lower interior cavity communicating with said lower opening;

an expandable and contractible socket collar disposed within said lower interior cavity for axial movement therewithin, said socket collar being of size and configuration to not pass through said lower opening of said central bore, said socket collar having a central opening configured to expandably receive a head of a component of a rod connector that is connectable to said rod of said existing spinal construct;

a crown disposed within said central bore between said upper portion and said socket collar, said crown being axially movable within said central bore independently of said socket collar, said crown having a lower end configured to contact said head of said component of said rod connector; and a retention insert disposed in said upper opening of said central bore between said top surface and said crown, said retention insert being secured to said extender body in a fixed position on said upper contact surface of said ledge allowing axial movement of said crown and said socket collar while retaining said crown and said socket collar within said central bore.

2. The modular rod extender of claim 1, wherein said retention insert is generally cylindrical having a central insert opening extending therethrough.

3. The modular rod extender of claim 2, wherein said retention insert includes internal threads in said central insert opening, said internal threads being configured to threadably receive external threads of a locking element.

4. The modular rod extender of claim 3, wherein said central bore includes internal threads in said upper opening along said upper portion, and wherein said retention insert includes external threads configured for threadable receipt into said internal threads of said upper opening of said central bore.

5. The modular rod extender of claim 3, wherein said retention insert is secured in said fixed position by welding.

6. The modular rod extender of claim 3, wherein said retention insert is a bushing.

7. The modular rod extender of claim 3, wherein a pair of opposing cutouts extend into said interior surface and at least said upper contact surface of said ledge is in communication with said upper opening, and wherein a pair of lobes project outwardly radially oppositely from said crown, said lobes extending into said cutouts and preventing rotation of said crown relative to said extender body.

8. The modular rod extender of claim 7, wherein said cutouts extend through said upper contact surface and said lower surface, said lower contact surface being in communication with said lower interior cavity.

9. The modular rod extender of claim 8, wherein said lower contact surface serves as a stop surface to limit axial movement of said socket collar within said lower interior cavity.

10. The modular rod extender of claim 9, wherein said lower interior cavity has at least one region of dimension wider than the dimension of said lower opening to allow expansion of said socket collar within said lower interior cavity.

11. The modular rod extender of claim 10, wherein said lower interior cavity has three regions each being of dimension wider than the dimension of said lower opening.

12. The modular rod extender of claim 1, wherein said socket collar comprises a ring of generally circular configuration having a generally circular central opening.

13. The modular rod extender of claim 12, wherein said ring is split defined by a gap that extends angularly through said ring.

14. The modular rod extender of claim 1, wherein said extension rod is attached to said extender body by a rod attachment feature.

15. The modular rod extender of claim 1, wherein said extender body and said extension rod are formed as an integral, one-piece member.

16. A modular rod extender for extending a rod in an existing spinal construct, formed by a process comprising the steps of:

providing an extender body comprising a modular attachment feature at one end and an extension rod extending from an opposite end, said modular attachment feature having a central bore extending along an axis through a top surface and a bottom surface of said extender body, said central bore being defined by an interior surface, a pair of opposing cutouts being formed into said interior surface, said central bore having a lower portion and an upper portion, said upper portion having an upper opening adjacent said top surface, said lower portion having a lower opening adjacent said bottom surface and a lower interior cavity communicating with said lower opening, said extender body including a ledge extending radially interiorly therewithin, said ledge including an interior surface defining said central bore, said ledge including an upper contact surface facing said upper portion of said central bore and a lower surface facing said lower portion of said central bore, said ledge having a pair of cutouts extending into said ledge through at least said upper contact surface and in communication with said upper opening;

introducing into said central bore through said upper opening of said upper portion of said central bore in a top loading process an expandable and contractible socket collar and disposing said socket collar into said lower interior cavity for axial movement therewithin, said socket collar being of size and configuration to not pass through said lower opening of said central bore, said socket collar having a central opening configured to expandably receive a head of a component of a rod connector that is connectable to said rod of said existing spinal construct;

introducing into said central bore through said upper portion of said central bore in a top loading process a crown and disposing said crown into said central bore between said upper portion and said socket collar, said crown being axially movable within said central bore independently of said socket collar, a pair of lobes projecting outwardly radially oppositely from said crown, said lobes extending into said cutouts and preventing rotation of said crown relative to said extender body, said crown having a lower end configured to forcibly engage said head of said component and wedge said head between said crown and said socket collar within said lower interior cavity of said extender body to thereby lock said extender body and said rod connector together.

17. The modular rod extender of claim 16 formed by a process comprising the further steps of:

introducing into said central bore through said upper portion of said central bore in a top loading process a retention insert and disposing said retention insert into said central bore between said top surface and said crown on said upper contact surface; and securing said retention insert to said extender body in a fixed position on said upper contact surface allowing axial movement of said crown and said socket collar within said central bore while retaining said crown and said socket collar within said central bore.

18. The modular rod extender of claim 17, wherein the step of introducing said retention insert includes the sub-step of placing said retention insert on said upper contact surface to cover said lobes of said crown within said cut-outs to thereby effectively retain said crown and said socket collar within said central bore.

19. A modular apparatus for extending a rod in an existing spinal construct, comprising:
    a rod connector comprising an attachment portion having an opening for receipt of a portion of said rod of said existing spinal construct, an elongate post projecting from said rod connector including a head having a partial spherical surface;
    a modular rod extender for extending a rod in an existing spinal construct, comprising an extender body comprising a modular attachment feature at one end and an extension rod extending from an opposite end, said modular attachment feature comprising:
    a) a central bore extending along an axis through a top surface and a bottom surface of said extender body, said central bore having a lower portion and an upper portion, said lower portion having a lower opening adjacent said bottom surface and a lower interior cavity communicating with said lower opening, said upper portion having an upper opening adjacent said top surface, said extender body including a ledge extending radially interiorly therewithin, said ledge including an interior surface defining said central bore, said ledge including an upper contact surface facing said upper portion of said central bore and a lower surface facing said lower portion of said central bore, said central bore being defined by said interior surface, a pair of opposing cutouts being formed into said interior surface of said ledge and through at least said upper contact surface, said cutouts being in communication with said upper opening, said lower opening being configured to receive therethrough said head of said elongate post and into said lower interior cavity;
    b) an expandable and contractible socket collar disposed within said lower interior cavity for axial movement therewithin, said socket collar being of size and configuration to not pass through said lower opening of said central bore, said socket collar having a central opening configured to expandably receive said head of said elongate post as said head extends into said lower interior cavity;
    c) a crown disposed within said central bore between said upper portion and said socket collar, said crown being axially movable within said central bore independently of said socket collar, said crown having a lower end configured to contact said head of said elongate post, a pair of lobes projecting outwardly radially oppositely from said crown, said lobes extending into said cutouts and preventing rotation of said crown relative to said extender body; and
    d) a retention insert disposed in said central bore between said top surface and said crown, said retention insert being secured to said extender body in a fixed position allowing axial movement of said crown and said socket collar while retaining said crown and said socket collar within said central bore; and
    a locking element insertable into said central bore, said locking element being configured to engage an upper end of said crown and cause said crown to forcibly engage said head of said elongate post and wedge said head between said crown and said socket collar within said lower interior cavity of said extender body to thereby lock said modular rod extender and said rod connector together.

20. The modular apparatus of claim 19, wherein said elongate post is movably supported by said rod connector to engage said rod and to secure said rod and said rod connector together upon such movement.

21. The modular apparatus of claim 19, wherein said extension rod has a longitudinal axis axially aligned with extender body and said central bore.

22. The modular apparatus of claim 19, wherein said extension rod has a longitudinal axis axially offset relative to said extender body and said central bore.

23. A modular rod extender for extending a rod in an existing spinal construct, formed by a process comprising the steps of:
    providing an extender body comprising a modular attachment feature at one end and an extension rod extending from an opposite end, said modular attachment feature having a central bore extending along an axis through a top surface and a bottom surface of said extender body, said central bore being defined by an interior surface, said central bore having a lower portion and an upper portion, said lower portion having a lower opening adjacent said bottom surface and a lower interior cavity communicating with said lower opening;
    introducing into said central bore through said upper portion of said central bore in a top loading process an expandable and contractible socket collar and disposing said socket collar into said lower interior cavity for axial movement therewithin, said socket collar being of size and configuration to not pass through said lower opening of said central bore, said socket collar having a central opening configured to expandably receive a head of a component of a rod connector that is connectable to said rod of said existing spinal construct;
    introducing into said central bore through said upper portion of said central bore in a top loading process a crown and disposing said crown into said central bore between said upper portion and said socket collar, said crown being axially movable within said central bore independently of said socket collar, said crown having a lower end configured to forcibly engage said head of said component;
    introducing into said central bore through said upper portion of said central bore in a top loading process a retention insert, said retention insert having a central insert opening, disposing said retention insert into said central bore between said top surface and said crown, and securing said retention insert to said extender body in a fixed position allowing axial movement of said crown and said socket collar within said central bore while retaining said crown and said socket collar within said central bore; and then
    introducing a locking element into said central insert opening in a top loading process, said locking element being configured to engage an upper end of said crown and cause said crown to move and wedge said head between said crown and said socket collar within said lower interior cavity of said extender body to thereby lock said extender body and said rod connector together.

24. The modular rod extender of claim 23, wherein said extender body includes a ledge extending radially interiorly therewithin, said ledge including said interior surface defining said central bore, said ledge further including an upper contact surface facing said upper portion of said central bore and a lower surface facing said lower portion of said central bore, and wherein the step of introducing said retention insert into said central bore includes the sub-step of placing said retention insert to bottom out on said upper contact surface.

25. The modular rod extender of claim 24, wherein said ledge includes a pair of opposing cutouts that extend into said interior surface and at least through said upper contact surface, said cutouts being in communication with said upper opening, and wherein said crown includes a pair of lobes projecting outwardly radially oppositely from said crown, and wherein the step of introducing said crown into said central bore includes the sub-step of placing said lobes of said crown into the respective cutouts of said ledge.

26. The modular rod extender of claim 25, wherein the step of introducing said retention insert into said central bore includes the further sub-step of placing said retention insert on said upper contact surface to cover said lobes of said crown within said cut-outs to thereby effectively retain said crown and said socket collar within said central bore.

27. The modular rod extender of claim 26, wherein the step of introducing said retention insert into said central bore includes the further sub-step of immovably fixing said retention member to said extender body.

28. The modular rod extender of claim 23, wherein said retention insert includes internal threads in said central insert opening, and wherein locking element includes external threads, and wherein the step of introducing said locking element into said central inset opening includes the further sub-step of threading said locking element into said retention insert.

* * * * *